United States Patent [19]

Manning

[11] 4,026,920

[45] May 31, 1977

[54] CHROMIUM MODIFIED MANGANESE FERRITE OXIDATIVE DEHYDROGENATION CATALYSTS

[75] Inventor: Harold E. Manning, Houston, Tex.

[73] Assignee: Petro-Tex Chemical Corporation, Houston, Tex.

[22] Filed: July 2, 1974

[21] Appl. No.: 485,306

Related U.S. Application Data

[60] Division of Ser. No. 289,177, Sept. 14, 1972, Pat. No. 3,859,375, which is a continuation-in-part of Ser. No. 78,956, Oct. 7, 1970, Pat. No. 3,751,385.

[52] U.S. Cl. .............................. 252/470; 252/447
[51] Int. Cl.$^2$ ........................................ B01J 23/64
[58] Field of Search ........................... 252/447, 470

[56] References Cited

UNITED STATES PATENTS

| | | |
|---|---|---|
| 2,683,123 | 7/1954 | Schwegler et al. ............... 252/470 |
| 3,205,179 | 9/1965 | Soderquist et al. ............... 252/447 |
| 3,666,684 | 5/1972 | Koslosky ........................... 252/415 |
| 3,666,687 | 5/1972 | Croce et al. ................... 260/680 E |
| 3,670,042 | 6/1972 | Croce et al. ................... 260/680 E |
| 3,716,589 | 2/1973 | Kotanigawa et al. ............. 252/470 |
| 3,751,385 | 8/1973 | Manning .......................... 252/470 |
| 3,751,512 | 8/1973 | Woskow et al. ............... 260/680 E |
| 3,859,375 | 1/1975 | Manning .......................... 252/470 |

*Primary Examiner*—Patrick P. Garvin
*Assistant Examiner*—John P. Sheehan
*Attorney, Agent, or Firm*—Kenneth H. Johnson; N. Elton Dry

[57] ABSTRACT

The presence of 0.05 to 0.4 atom of chromium per atom of manganese in a manganese ferrite oxidative dehydrogenation catalyst improves the yields from oxidative dehydrogenation reactions employing such catalyst. A chromium modified manganese ferrite catalysts containing from 1 to 20 weight percent carbon is also disclosed.

6 Claims, No Drawings

CHROMIUM MODIFIED MANGANESE FERRITE OXIDATIVE DEHYDROGENATION CATALYSTS

This application is a division of Ser. No. 289,177, filed Sept. 14, 1972 now U.S. Pat. No. 3,859,375 which is a continuation-in-part of co-pending application Ser. No. 78,956 filed on Oct. 7, 1970, now U.S. Pat. No. 3,751,385 and the entire contents thereof are incorporated herein by reference.

This invention relates to oxidative dehydrogenation of organic compounds having a least one

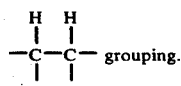
grouping.

More particularly the invention relates to the use of manganese ferrite catalyst in such oxidative dehydrogenation. Specifically the invention relates to manganese ferrite catalysts containing from 0.05 to 0.4 atom of chromium per atom of manganese.

It is known to dehydrogenate organic compounds by contacting the compounds to be dehydrogenated at an elevated temperature preferably in the presence of catalysts. One method of dehydrogenation is known as oxidative dehydrogenation. According to this process, hydrogen released from the organic compounds reacts with oxygen to form water. One of the principal defects in oxidative dehydrogenation reactions is that quite often the reactions are unselective and oxygenated compounds are formed instead of the desired dehydrogenated compounds. These non-selective reactions are particularly evident when the compound to be dehydrogenated contains three or more carbon atoms. For example, when methyl butene is reacted with oxygen, a variety of products other than isoprene are possible as hydrocarbons and oxygenated hydrocarbons of various general mixtures may result. Also, combustion of the hydrocarbon may result in the formation of CO, $CO_2$, and water.

It is therefore one of the principal objectives of this invention to provide a process and catalyst wherein the organic compound is dehydrogenated preferably to a product having the same number of carbon atoms at a high level of conversion and selectivity. Another principal objective is to provide a process wherein the catalyst has long catalyst life. Other objectives of this invention are to provide a process wherein it is possible to have substantial quantities of steam present in the dehydrogenation zone, a high over-all throughput and a low contact time in the dehydrogenation zone and a process which has good control of reaction temperature. These and other objectives may be achieved by the process of this invention.

Briefly stated, one aspect of the present invention is an oxidative dehydrogenation catalyst comprising a manganese ferrite containing a minor amount of chromium. Generally the manganese ferrite will contain from about 0.05 to 0.4 atom of chromium per atom of manganese contained in the catalyst and preferably about 0.05 to 0.2 atom of chromium per atom of manganese. In another embodiment of the present invention, the catalyst comprises manganese ferrite, 0.05 to 0.5 atoms of chromium per atom of manganese and about 1 to 20 weight percent carbon black. In a preferred embodiment, the carbon black is present in a range of about 1 to 15 weight percent and more preferably about 2 to 10 weight percent.

In addition to chromium and carbon black the catalyst may also contain binding agents or fillers, but the chromium, carbon black and the binders and fillers will not ordinarily exceed about 50 percent or 60 percent by weight of the catalysts and the described catalytic compositions will preferably constitute the main active constituent. These binding agents and fillers will preferably be essentially inert. Preferred catalysts are those that have a lease 25 or preferably 50 weight percent of the defined catalyst actives. Also preferably iron will constitute at least 50 atomic weight percent of the cations in the catalyst. Unless stated otherwise, the compositions in this application are the main active constituents of the dehydrogenation process during dehydrogenation and any ratios and percentages refer to the surface of the catalyst in contact with the gaseous phase during dehydrogenation.

The catalysts of this invention comprises manganese ferrite produced in a particular manner. Manganese ferrite comprises a complex crystalline structure comprising manganese, iron and oxygen. According to this invention superior catalysts can be formed by producing the manganese ferrite by reacting an active compound of iron with an active compound of manganese. By active compound is meant a compound which is reactive under the conditions to form the ferrite.

The starting materials may be such as oxides, hydroxides, or salts including oxalates, acetates, formates, sulfates, nitrates, halides, hydrates, and so forth. Suitable manganese compounds are such as manganese oxalate, manganese hydroxide, manganese nitrate, manganese carbonate, manganese salts of aliphatic monocarboxylic acids of 1 to 5 carbon atoms, manganese sulfates, salts of aliphatic alcohols of 1 to 5 carbon atoms, hydrates thereof and mixtures thereof. The same classes of iron compounds may be employed such as iron nitrate, etc. The inorganic salts give excellent results.

The iron and manganese precursor components and the chromium containing component can be combined in any conventional manner which will provide an intimate mixture, for example, manganese oxide, iron oxide and chromium component can be mixed in a slurry or dry mixed. One component can be deposited on another or the precursor components can be coprecipitated.

One procedure for forming the catalysts is to prepare an aqueous mixture of the precursor salts and thereafter this mixture can then be precipitated by mixing with a basic reactant to precipitate the precursor of the ferrite. Any suitable base may be employed but those containing unwanted cations will, of course, be less desirable. Volatile bases such as ammonium hydroxide or carbonate may be employed.

The temperature used for ferrite formation may be varied, depending somewhat upon the particular starting materials and upon the conditions present during ferrite formation. At any rate, superior catalysts are produced at temperatures of from high enough to form the ferrite to 800° C or less. Still better catalysts are ordinarily produced at temperatures of less than 700° C. Suitable temperatures of reaction are such as between about 400° to 800° C with a preferred range being from between aabout 500 to 700° C.

Another factor in producing superior catalysts is the rate of heating of the reactants to form the ferrite. Here again the rate of heating will be dependent upon the particular reactants and conditions employed, but better results are generally obtained when the reactants are heated at a rate of no greater than about 150° C per minute and still better results are ordinarily obtained when the rate is no greater than about 100° C per minute.

The ferrites are preferably prepared in an atmosphere containing little or no oxygen. Preferably the atmosphere will contain less oxygen than air, i.e., less than about 15 mole percent oxygen. More preferably the calcining atmosphere will be substantially free of oxygen. Suitable atmospheres are gases such as nitrogen, helium, argon, neon, krypton, xenon and the like or mixtures thereof.

Improved manganese ferrite compositions may be obtained by utilizing halogen or halogen compounds during the formation of the ferrite. The use of halogen or halogen compounds in this manner is claimed in U.S. Pat. No. 3,567,793, issued Mar. 2, 1971. An example of the use of a halogen would be the addition of manganese chloride to the reactants prior to the formation of the ferrite. Normally, chlorine is the preferred halogen so used.

The manganese ferrite compositions of this invention may also comprise additives. Phosphorus, silicon or mixtures thereof are examples of additives. For instance, phosphorus and/or silicon amy suitably be present in an amount of from 0.2 to 20 weight percent based on total weight of the atoms of iron and manganese. These ingredients may contribute e.g. to the stability of the compositions. The silicon, phosphorus or other additives may be added at various stages of the preparation of the composition, or may be added to the already formed manganese ferrite. Any suitable compounds may be employed such as phosphoric acid, phosphorus pentoxide, ethyl phosphate, ammonium phosphate, silicon halides, etc.

The chromium is incorporated into ferrite preferably by combining a reactive chromium compound with the reactive iron and manganese compounds prior to reacting to form the ferrite. Suitable reactive materials are chromium oxide, chromium oxalate, chromium acetate, chromium sulfate and the like, as previously described for the iron and manganese starting material.

The carbon, when used, is preferably incorporated by combining the reactive iron, manganese, and chromium compounds with the carbon prior to reacting to form the ferrite.

The chromium modified manganese ferrite compositions may be reduced with a reducing gas prior to use in the process of dehydrogenation. Example of reducing gases are hydrogen or hydrocarbons. For example, the manganese ferrite compositions may be reduced with e.g. hydrogen at a temperature of at least 250° C with the temperature of reduction generally being no greater than 850° C. By reducing gas is meant a gas that will react with oxygen under the conditions of reduction. However, it is one of the advantages of this invention that the manganese ferrites prepared according to this invention may not require reduction prior to use in the dehydrogenation reaction.

According to this invention it has been found that the preferred manganese ferrite compositions exhibit a certain type of X-ray diffraction pattern. The preferred compositions do not have as sharp X-ray diffraction reflection peaks as would be found, e.g., in a high crystalline material having the same chemical composition. Instead, the preferred catalyst of this invention exhibit reflection peaks which are relatively broad. The degree of sharpness of the reflection peak may be measured by the reflection peak band width at half height (W $h/2$). In other words, the width of the reflection peak as measured at one-half of the distance to the top of the peak is the "band width at half height". The band width at half height is measured in units of °2 theta. Techniques for measuring the band widths are discussed, e.g., in Chapter 9 of Klug and Alexander, X-ray Diffraction Procedures, John Wiley and Son, N.Y., 1954.

The process of this invention may be applied to the dehydrogenation of a great variety of organic compounds to obtain the corresponding unsaturated derivative thereof. Such compounds normally will contain from 2 to 20 carbon atoms, at least one

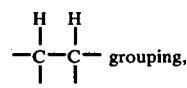

a boiling point below about 350° C, and such compounds may contain other elements, in addition to carbon and hydrogen such as oxygen, halogens, nitrogen and sulphur. Preferred are compounds having from 3 to 12 carbon atoms, and especially preferred are compounds of 3 to 6 or 8 carbon atoms.

Among the types of organic compounds which may be successfully dehydrogenated to the corresponding unsaturated derivative by means of the novel process of this invention are nitriles, amines, alkyl halides, ethers, esters, aldehydes, ketones, alcohols, acids, alkyl aromatic compounds, alkyl heterocyclic compounds, cycloalkanes, alkanes, alkenes, and the like. Illustration of dehydrogenations include propionitrile to acrylonitrile, propionaldehyde to acrolein, ethyl chloride to vinyl chloride, methyl isobutyrate to methyl methacrylate, 2 or 3-chlorobutene-1 or 2,3-dichlorobutane to chloroprene, ethyl pyridine to vinyl pyridine, ethylbenzene to styrrene, isopropylbenzene to α-methyl styrene, ethylcyclohexane to styrene, cyclohexane to benzene, propane to propylene, isobutane to isobutylene, n-butane to butene and butadiene-1,3, butene to butadiene-1,3 and vinyl acetylene, methyl butene to isoprene, cyclopentane to cyclopentene and cyclopentadiene-1,3, n-octane to ethyl benzene and ortho-xylene, monomethylheptanes to xylenes, propane to propylene to benzene, ethyl acetate to vinyl acetate, 2,4,4-trimethylpentane to xylenes, and the like. This invention may be useful for the formation of new carbon to carbon bonds by the removal of hydrogen atoms such as the formation of a carbocyclic compound from two aliphatic hydrocarbon compounds or the formation of a dicyclic compound from a monocyclic compound having an acyclic group. Examples of conversions are the conversion of n-heptane to toluene and propene to diallyl. Representative materials which are dehydrogenated by the novel process of this invention include ethyl toluene, alkyl chlorobenzenes, ethyl naphthalene, isobutyronitrile, propyl chloride, isobutyl chloride, ethyl fluoride, ethyl bromide, n-pentyl iodide, ethyl dichloride, 2,3-dichlorobutane, 1,3-dichlorobutane, 1,4-dichlorobutane, the chlorofluoroethanes, methyl pentane, methylethyl ketone, diethyl ketone, n-butyl alcohol, methyl propionate, and the like. This invention is particularly adapted to the preparation of vinylidene compounds containing at least one $CH_2 = C$ group, that is, a group containing a terminal methylene group attached by a double bond to a carbon atom, and having 2 to 12 carbon atoms by the dehydrogenation of compounds of the formula $CH_3$—$CH_2$—R wherein R is an organic radical of from 0 to 10 carbon atoms, preferably a hydrocarbon. Similarly, acetylenic compounds of the formula CH ≡ C— may be produced from the same starting materials.

Preferably oxygen is employed, suitably in an amount within the range of 0.2 to about 5.0 mols of oxygen per mol of organic compound to be dehydrogenated, preferably from 0.2 to 2.5 moles per mole. Generally, better results may be obtained if the oxygen concentration is maintained between about 0.25 and about 1.6 moles of oxygen per mole of organic compound to be dehydrogenated, such as between 0.35 and 1.2 moles of oxgen. The oxygen may be fed to the reactor as pure oxygen, as air, as oxygen-enriched air, oxygen mixed with diluents, and so forth. Based on the total gaseous mixture entering the reactor, good results are obtained with oxygen present in an amount from about 0.5 to 25 volume percent of the total gaseous mixture, such as in an amount from about 1 to 15 volume percent of the total. The total amount of oxygen utilized may be introduced into the gaseous mixture entering the catalytic zone or sometimes it has been found desirable to add the oxygen in increments, such as to differenct sections of the reactor. The above described proportions of oxygen employed are based on the total amount of oxygen used. The oxygen may be added directly to the reactor or it may be premixed, for example, with a diluent or steam. It is also within the scope of this invention to employ the described manganese compositions as the partial or sole source of oxygen used for oxidative dehydrogenation. For example, the manganese compositions may release oxygen to react with the organic compound during a dehydrogenation step and thereafter the manganese composition is regenerated by oxidation prior to another step where oxygen is released. Preferably such a process will have the manganese composition present as a moving bed.

It is one of the advantages of this invention that halogen may also be added to the reaction gases to give excellent results. The addition of halogen to the feed is particularly effective when the hydrocarbon to be dehydrogenated is saturated. The halogen present in the dehydrogenation zone may be either elemental halogen or any compound of halogen which would liberate halogen under the conditions of reaction. Suitable sources of halogen are such as hydrogen iodide, hydrogen bromide and hydrogen chloride; aliphatic halides, such as ethyl iodide, methyl bromide, 1,2-dibromo ethane, ethyl bromide, amyl bromide, and allyl bromide; cycloaliphatic halides, such as cyclohexylbromide; aromatic halides, such as benzyl bromide; halohydrins, such as ethylene bromohydrin; halogen substituted aliphatic acids, such as bromoacetic acid; ammonium iodide; ammonium bromide; ammonium chloride; organic amine halide salts, such as methyl amine hydrobromide; metal halides including molten halides; and the like. Mixtures of various sources of halogen may be used. The preferred sources of halogen are iodine, bromine, and chlorine, and compounds thereof, such as hydrogen bromide, hydrogen iodide, hydrogen chloride, ammonium bromide, ammonium iodide, ammonium chloride, alkyl halides of one to six carbon atoms and mixtures thereof, with the iodine and bromine compounds, especially the ammonium compounds, being particularly preferred. When terms such as halogen liberating materials or halogen materials are used in the specification and claims, this includes any source of halogen such as elemental halogens, hydrogen halides, or ammonium halides. The amount of halogen, calculated as elemental halogen, may be as little as about 0.0001 or less mole of halogen per mole of the organic compound to be dehydrogenated to as high as 0.2 or 0.5. The preferred range is from about 0.001 to 0.09 mole of halogen per mole of the organic compound to be dehydrogenated.

The temperature for the dehydrogenation reaction generally will be at least about 250° C, such as greater than about 300° C or 375° C, and the maximum temperature in the reactor may be about 650° C or 750° C or perhaps higher such as 900° C under certain circumstances. However, excellent results are obtained witin the range of or about 300° C to 575° C, such as from or about 325° C to or about 525° C. The temperatures are measured at the maximum temperature in the dehydrogenation zone. An advantage of this invention is that lower temperatures of dehydrogenation may be utilized than are possible in conventional dehydrogenation processes. Another advantage is that large quantities of heat do not have to be added to the reaction.

The dehydrogenation reaction may be carried out at atmospheric pressure, superatmospheric pressure or at sub-atmospheric pressure. The total pressure of the system will normally be about or in excess of atmospheric pressure, although sub-atmospheric pressure may also desirably be used. Generally, the total pressure will be between about 4 p.s.i.a. and about 100 or 125 p.s.i.a. Preferably, the total pressure will be less than about 75 p.s.i.a. and excellent results are obtained at about atmospheric pressure.

Preferably, the reaction mixture contains a quantity of stream, with the range generally being between about 2 and 40 moles of steam per mole of organic compound to be dehydrogenated. Preferably, steam will be present in an amount from about 3 to 35 moles per mole of organic compounds to be dehydrogenated and excellent results have been obtained within the range of about 5 to about 30 moles of steam per mole of organic compound to be dehydrogenated. The functions of the steam are several-fold, and the steam may not merely act as a diluent. Diluents generally may be used in the same quantities as specified for the steam.

The gaseous reactants may be conducted through the reaction chamber at a fairly wide range of flow rates. The optimum flow rate will be dependent upon such variables as the temperature of reaction, pressure, particle size, and whether a fluid bed or fixed bed reactor is utilized. Desirable flow rates may be established by one skilled in the art. Generally, the flow rates will be within the range of about 0.10 to 25 liquid volumes of the organic compound to be dehydrogenated per volume of dehydrogenation zone containing catalyst per hour (referred to as LHSV), wherein the volumes of organic compound are calculated at standard conditions of 0° C and 760 mm of mercury. Usually, the LHSV will be between 0.15 and about 5 to 10. For calculation, the volume of reactor containing catalyst is that volume of reactor space including the volume displaced by the catalyst. For example, if a reactor has a particular volume of cubic feet of void space, when that void space is filled with catalyst particles, the original void space is the volume of reactor containing catalyst for the purpose of calculating the flow rate. The gaseous hourly space velocity (GHSV) is the volume of the organic compound to be dehydrogenated in the form of vapor calculated under standard conditions of 0° C and 760 mm of mercury per volume of reactor space containing catalyst per hour. Generally, the GHSV will be between about 25 and 6400, and excellent results have been obtained between about 38 and 3800. Suitable contact times are, for example, from about 0.001 or higher to about 4 to 10 or 25 seconds, with particularly good results being obtained between 0.01 and 5 seconds. The contact time is calculated dwell time of the reaction mixture in the reaction mixture in the reaction zone, assuming the moles of product mixture are equivalent to the moles of feed mixture. For the purpose of calculation of contact times, the reaction zone is the portion of the reactor containing catalyst which is at a temperature of at least 250° C.

The dehydrogenation reactor may be of the fixed bed or fluid bed type. Conventional reactors for the production of unsaturated organic compounds by dehydrogenation are satisfactory. Excellent results have been obtained by packing the reactor with catalyst particles as the method of introducing thecatalytic surface. The catalytic surface may be introduced as such or it may be deposited on a carrier by methods known in the art such as by preparing an aqueous solution or dispersion of a catalytic material and mixing the carrier with the solution or dispersion until the active ingredients are coated on the carrier. If a carrier is utilized, very useful carriers are silicon carbide, aluminum oxide, pumice, and the like. Other known catalyst carriers may be employed. When carriers are used, the amount of catalyst on the carrier will suitably be between about 5 to 75 weight percent of the total weight of the active catalytic material plus carrier. Another method for introducing the required surface is to utilize as a reactor a small diameter tube wherein the tube wall is catalytic or is coated with catalytic material. Other methods may be utilized to introduce the catalytic surface such as by the use of rods, wires, mesh, or shreds, and the like, of catalytic material.

In the following examples the conversions, selectivities and yields are reported in mole percent. Otherwise, all percentages are weight percent unless expressed to the contrary. The apparatus used in the oxidative dehydrogenations consisted of a vertical fixed bed reactor containing thermocouples at spaced intervals throughout the bed. The temperature reported for each dehydrogenation is the maximum temperature in the bed. The effluent from the reactor was condensed and analyzed immediately by vapor phase chromatography.

EXAMPLE 1

Catalyst Preparation

The catalysts were prepared from the quantities of starting materials described in Table 1. The material were slurried together in distilled water for 20 minutes using a one gallon Waring blender. The slurry was dried in an oven at 100° C. The dried cake was screened to remove particles larger than 40 mesh and calcined in a Vycor combustion tube (using a $N_2$ atmosphere at 100 vols. of $N_2$/vol. of catalyst/hour) to the final calcination temperature of 600° C and held at this temperature for 1 hour.

TABLE I

| Materials | Catalyst A (Grams) | Catalyst B (Grams) | Catalyst C (Grams) | Catalyst D (Grams) |
|---|---|---|---|---|
| 1. $Fe_2O_3$* | 555 | 535 | 500 | 523 |
| 2. $M_nCO_3$ | 330 | 330 | 330 | 353 |
| 3. $MnCl_2 \cdot 4H_2O$** | 36 | 36 | 36 | 36 |
| 4. $Cr_2O_3$*** | 0 | 15.5 | 31 | 23 |
| 5. Distilled Water | 1300 | 1300 | 1300 | 1300 |
| 6. Carbon Black | 0 | 0 | 0 | 50 |

*Williams yellow hydrated $\alpha$-$Fe_2O_3$YLO-1788 assay 86–88% $Fe_2O_3$.
**Baker Analyzed Reagent Grade
***Baker (C.P.)

Portions of catalyst A, B, C, and D were each calcined at 600° C as indicated above. Portions of each of the calcined products were prepared for use by depositing 76 grams of the calcined product and 2.3 grams of 86% $H_3PO_4$ onto 145 grams of HCl leached 6–9 mesh AMC alumina. X-ray scan indicated that a manganese ferrite was the predominate material in each calcined product. The same amount of each catalyst was employed for the runs in Example 2 in the reactor as described.

EXAMPLE 2

Oxidative Dehydrogenation

In runs 1–3, a feed of isoamylenes (88% 2-methyl butene-2 and 8% 2-methyl butene-1) was fed at 1.5 LHSV, mole ratio of steam/$0_2$hydrocarbon of 30/0.9/1. In run 4, a feed of isoamylenes 85.4% 2-methyl butene-1, 0.7% pentane, 2.9% isopentane, 2.8% other $C_5$ and 0.1% heavy ends was fed at 1.5 LHSV, mole ratio of steam/$0_2$/hydrocarbon of 30/0.9/1. In Table II the catalysts, maximum temperatures and results for each run are reported.

TABLE II

| Run | Catalyst | Temp. ° F Max. | Isoprene Mole % Conversion | Selectivity | Yield |
|---|---|---|---|---|---|
| 1 | A | 970 | 58 | 90 | 52 |
| 2 | B | 930 | 61 | 90 | 54.9 |
| 3 | C | 950 | 62 | 88 | 54.5 |
| 4 | D | 990 | 63 | 86.6 | 54.6 |

The invention claimed is:

1. An oxidative dehydrogenation catalyst consisting essentially of manganese ferrite containing from 0.05 to 0.4 atom of chromium per atom of manganese.

2. The catalyst according to claim 1 wherein the manganese ferrite contains up to 0.4 atom of chromium per atom of manganese in the crystalline lattice of the ferrite.

3. The catalyst according to claim 2 wherein the atom ratio of chromium to manganese in the ferrite is in the range of 0.05 : 1 to 0.2 : 1.

4. The oxidative dehydrogenation catalyst according to claim 1 prepared by intimately contacting an active compound of iron with an active compound of manganese with a reactive compound of chromium in an atom ratio of Cr to Mn in the range of 0.05 : 1 to 0.2 : 1 at a temperature high enough to form a ferrite to 800° C said iron, manganese and chromium compounds being oxides, hydroxides or salts.

5. The oxidative dehydrogenation catalyst according to claim 4 wherein said chromium compound is chromium oxide, chromium oxolate, chromium acetate or chromium sulfate.

6. The oxidative dehydrogenation catalyst according to claim 4 wherein said chromium compound is chromium oxide.

* * * * *